United States Patent [19]
Welker

[11] Patent Number: 5,996,425
[45] Date of Patent: *Dec. 7, 1999

[54] VANISHING HEAD SAMPLE CYLINDER

[75] Inventor: Brian H. Welker, Sugar Land, Tex.

[73] Assignee: Welker Engineering Company, Sugar Land, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/864,159

[22] Filed: May 28, 1997

[51] Int. Cl.$^6$ .................................................. G01N 1/14
[52] U.S. Cl. .................................... 73/864.62; 73/864.63
[58] Field of Search ........................... 73/864.61, 864.62, 73/864.63, 864.51, 863.81, 864.34, 863.83

[56] References Cited

U.S. PATENT DOCUMENTS

| | | | |
|---|---|---|---|
| 3,945,770 | 3/1976 | Welker | 417/401 |
| 4,403,518 | 9/1983 | Welker | 73/864.34 |
| 4,403,519 | 9/1983 | Welker | 73/864.62 |
| 4,440,032 | 4/1984 | Welker | 73/863.84 |
| 4,459,865 | 7/1984 | Welker | 73/864.62 |
| 4,470,773 | 9/1984 | Welker | 417/479 |
| 4,525,127 | 6/1985 | Welker | 417/479 |
| 4,537,058 | 8/1985 | Luper | 73/864.87 |
| 4,841,785 | 6/1989 | Welker | 73/863.84 |
| 4,862,754 | 9/1989 | Nimberger | 73/864.62 |
| 4,922,764 | 5/1990 | Welker | 73/864.62 |
| 5,109,712 | 5/1992 | Nimberger et al. | 73/864.52 |

*Primary Examiner*—Hezron Williams
*Assistant Examiner*—Nashmiya Fayyaz
*Attorney, Agent, or Firm*—Herzog, Crebs & McGhee, L.L.P.

[57] ABSTRACT

A sample cylinder for holding natural gas or other fluid samples for analysis which can completely clear itself of one sample before being filled with a subsequent sample. The piston is adapted to receive an elastomeric head which is preferably concave to the end cap. The end cap is also preferably sloped downward toward the outlet. When the piston head contacts the end cap, contact begins near the cylinder body wall and progresses inward to the outlet. The end cap is adapted to receive an elastomeric gasket seal instead of an o-ring. No spaces are left between the end cap and the cylinder body which could retain sample fluid.

11 Claims, 3 Drawing Sheets

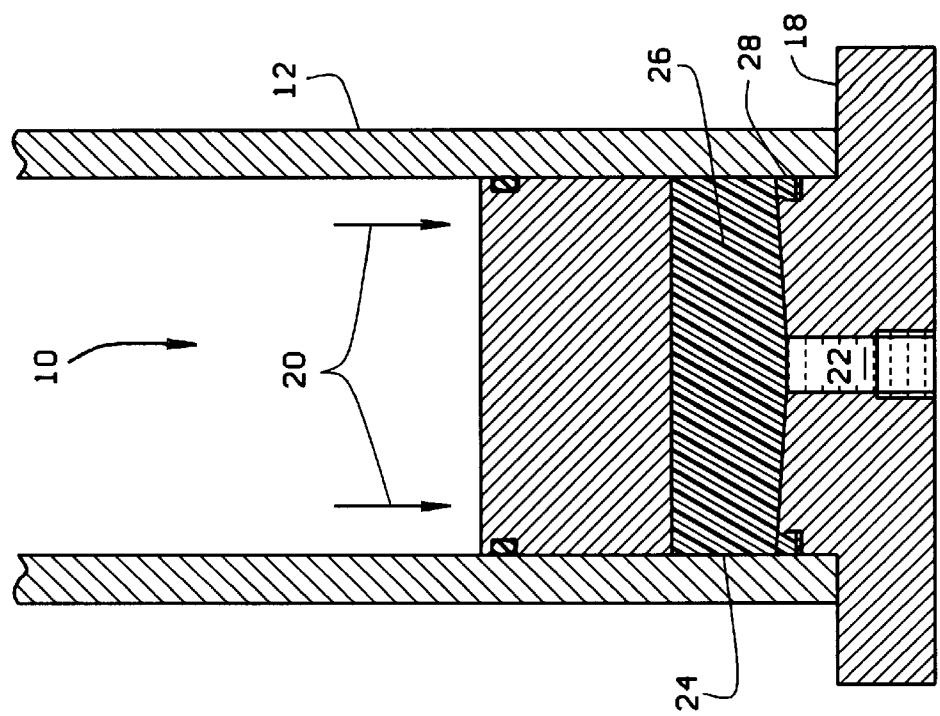
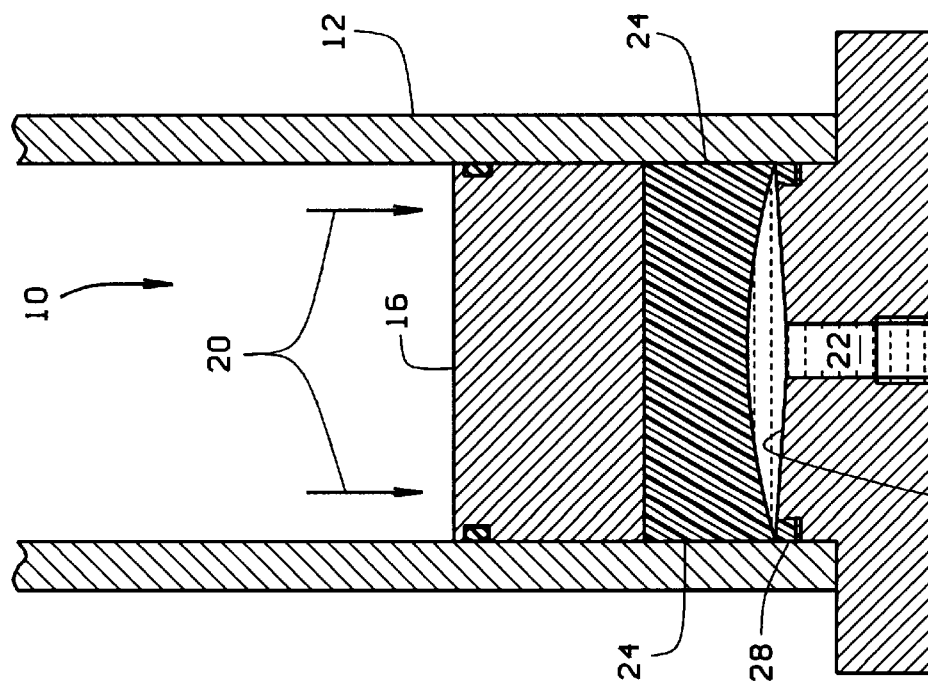

VANISHING HEAD SAMPLE CYLINDER

FIELD OF THE INVENTION

The present invention relates to gas sample cylinders, and more particularly to a sample cylinder which can purge all fluids located therein between samples.

BACKGROUND OF THE INVENTION

It is often desirable to accumulate a sample of a fluid, such as natural gas, in cylinders for later analysis. Several sample cylinders have been invented over time, such as those described in U.S. Pat. Nos. 4,922,764 and 4,459,865 both having common inventorship herewith. A problem exists with these and other previous designs when it is necessary to purge the entire contents from the cylinder to avoid even minute contamination of subsequent samples.

Furthermore, sample cylinders typically have end caps that fit into the cylinder bodies. To prevent leakage of the sample, o-rings are placed between the sample cylinder and the end cap. O-rings leave behind gaps between the o-ring groove of the end cap and the o-ring itself. These gaps can hold trace amounts of a sample, which can slightly contaminate subsequent samples.

It is therefore an object of the present invention to provide a sample cylinder with the ability to purge the entire contents thereof when desired by the user.

It is further an object of the present invention to provide a sample cylinder without gaps between the cylinder body and the end cap.

Other objects of the invention will become apparent from the specification described herein below.

SUMMARY OF THE INVENTION

In accordance with the objects listed above, there is provided a vanishing head sample cylinder comprising a hollow cylindrical body open at one end containing a sealably mounted, axially movable piston therein, an end cap covering the open end of the cylindrical body, said end cap containing an outlet providing fluid communication between the exterior of the cylinder. The piston is adapted to have an evacuating portion nearest the head thereof, the head, in turn, positioned nearest the end cap. The evacuating portion of the piston voids the interior of the sample cylinder of the sampled material.

The present sample cylinder incorporates three main design improvements that allow it to be purged completely of sampled material. The first improvement involves the addition of an elastomer affixed to the piston head, the elastomer being preferably concave. The previously flat inner face of the end cap should be sloped slightly. Lastly, an elastomeric seal that fits between the cylinder wall and the end cap preferably replaces the o-ring, thereby leaving no gaps into which gas may be trapped.

According to one aspect of the present invention, the cylinder piston is adapted to receive an elastomer on the head thereof. The elastomer should be cupped, and as the piston contacts the end cap, the cupped portion will disappear, i.e. the elastomer will conform to the shape of the end cap, similar to the technique used in samplers shown in U.S. Pat. No. 3,945,770 to Welker and several subsequent patents. A major difference between the application of vanishing heads in pumps such as samplers and a sample cylinder is the head in a sample cylinder must take up the entire cross section of the interior of the cylinder.

According to another aspect of the present invention, the face of the end cap is sloped approximately 3° toward the outlet. This creates a frusto-conical shape which aids the piston head in evacuating the entire cylinder.

According to yet another aspect of the present invention, the end cap is sealed with an elastomeric gasket instead of an o-ring. The end cap, therefore a groove for an o-ring which can retain portions of the sample fluid even after the piston head reaches the end cap is eliminated.

BRIEF DESCRIPTION OF THE DRAWINGS

So that the manner in which the above-identified features, advantages, and objects of the present invention are attained and can be understood in detail, a more particular description of the invention, briefly summarized above, may be had by reference to the embodiment thereof which is illustrated in the appended drawings.

It is noted, however, that the appended drawings illustrate only a typical embodiment of this invention and is therefore not to be considered limiting of its scope, for the invention may admit to other equally effective embodiments. Reference the appended drawings, wherein:

FIG. 3 is an enlarged cross-sectional view of an end portion of the present sample cylinder discharging the sample fluid as the piston head makes first contact with the end cap;

FIG. 4 is an enlarged cross-sectional view of an end portion of the present sample cylinder after the cylinder has been completely evacuated up to the end cap;

DETAILED DESCRIPTION OF THE DRAWINGS

Figure 1:
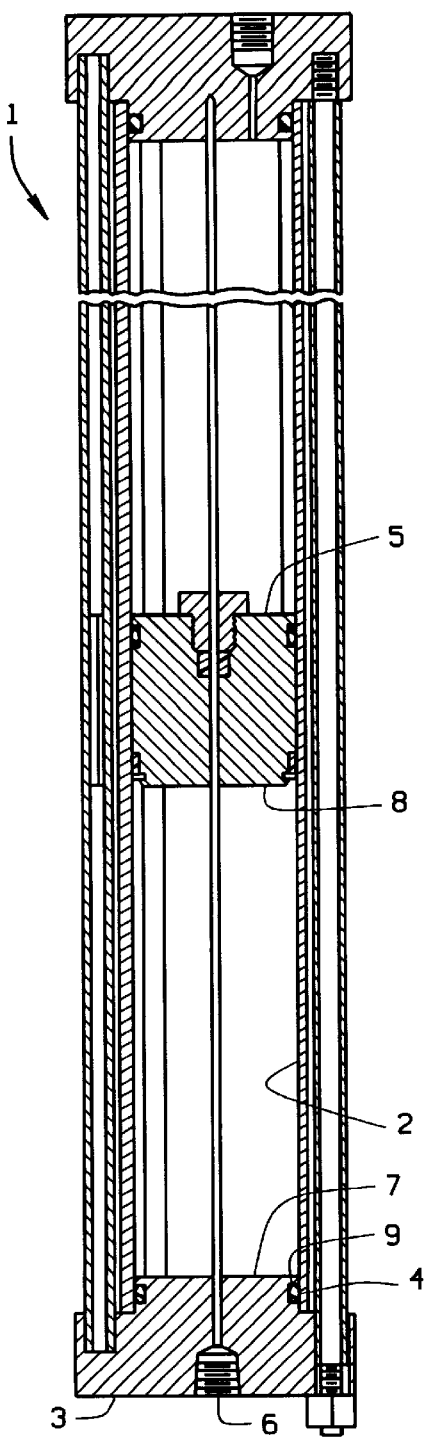
FIG. 1 is a cross-sectional view of a prior art sample cylinder.

FIG. 1, generally shows a prior art conventional sample cylinder 1. The sample cylinder 1 is for holding samples of gaseous fluids for analysis, such as natural methane gas. The sample cylinder 1 is comprises a cylinder body 2 and an end cap 3. To prevent leakage an o-ring 4 is disposed between the cylinder body 2 and the end cap 3. To clear the sample cylinder 1, a piston 5 forces the gas downward and through an outlet opening 6 in the end cap 3. The inner face 7 of the end cap 3 and the head 8 of the piston 5 are both flat. When the sample cylinder purges the sample fluid, portions thereof remain behind which is undesirable. Particularly, some fluid remains in the groove 9 of the end cap 3 that holds the o-ring 4.

Figure 2:
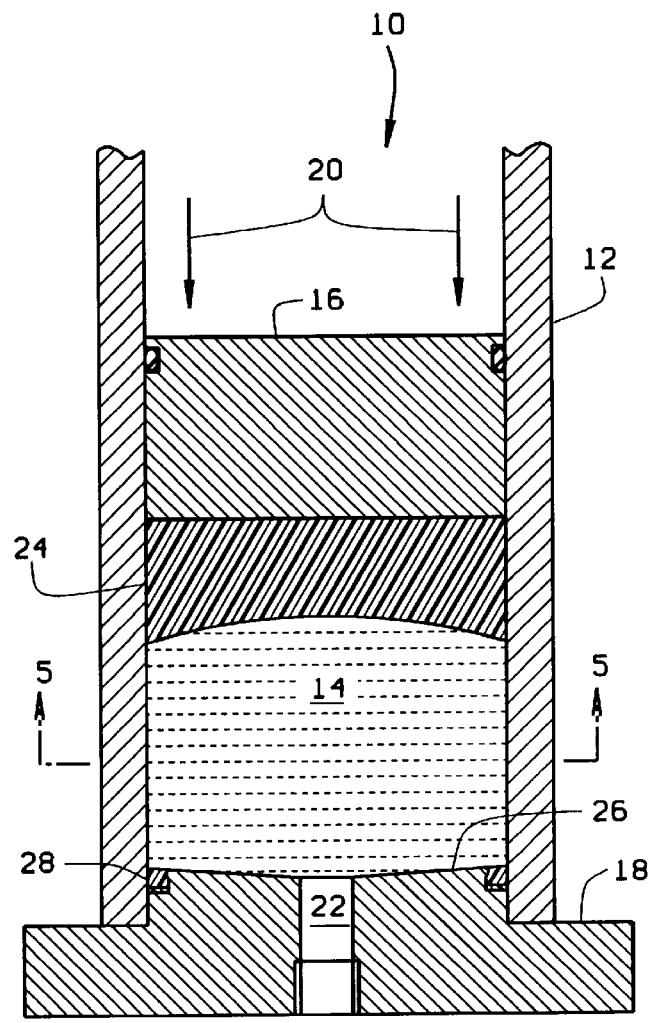
FIG. 2 is an enlarged cross-sectional view of an end portion of the present sample cylinder filled with a sample fluid.

Referring now to FIG. 2, an end portion of the present sample 10 cylinder is shown generally. The cylinder body 12 is the same as that used in the prior art sample cylinder 1. The sample fluid 14 is held in the area between the piston 16 and the end cap 18. To clear the sample cylinder 10 of one sample and prepare it for the next sample, a force (represented by the arrows 20) is applied to the piston 16 and the fluid 14 exits the end cap 18 through an outlet 22 as the piston 16 moves through the sample cylinder 10. The piston 16 is fitted with a special head 24. The piston head 24 is made of an elastomer. Any type of elastomer may be used, such as most types of rubbers, natural or synthetic, so long as the material used is inert with respect to sample fluid 14 to be collected, usually natural gas. The preferred embodiment uses Viton®, manufactured by E. I. DuPont de Nemours & Co. of Wilmington, Del., for the piston head 24.

Figure 5:
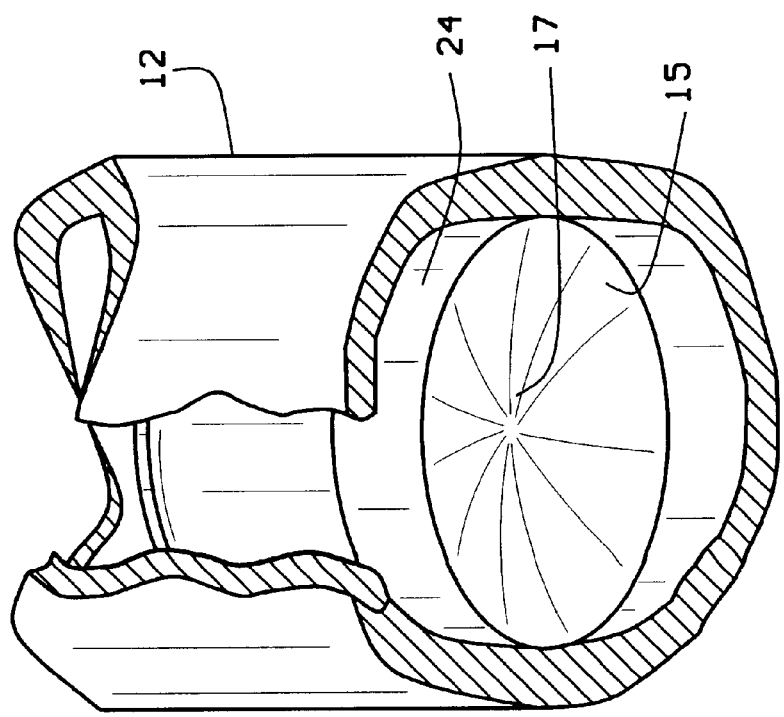
FIG. 5 is an isometric cutaway of the piston head of the present sample cylinder taken from line 5—5 of FIG. 2.

The portion of the piston head 24 which contacts the end cap 18 is preferably concave, though a completely flat surface may work as well so long as the inner face 26 of the end cap 18 is sloped as discussed below. The concave nature of the piston head 24 can best be seen in FIG. 5.

FIG. 3 shows the piston head 24 first making contact with the end cap 18. To further aid the piston head 24, the inner face 26 of the end cap 18 is preferably sloped slightly downward toward the outlet 22. The angle of the slope should only be about 3°, though more or less of a slope will also work. If a concave piston head 24 is utilized, the inner face 26 of the end cap 18 need not be sloped at all. In the preferred embodiment, however, the piston head 24 is concave and the inner face 26 of the end cap 18 is nonetheless sloped.

FIG. 4 shows the piston head 24 making complete contact with the end cap 18, completely clearing the inside of the sample cylinder 10. Note that the elastomeric nature of the piston head 24 causes the concave section thereof to completely disappear as it contacts the end cap 18. Contact between the piston head 24 and the end cap 18 begins at the outside near the cylinder body 12, and as the force 20 continues to be applied, the contact between the piston head 24 and the end cap 18 progresses toward the center of the inner face 26 of the end cap 18 where the outlet 22 is located. Thus, the outer portion 15 (see FIG. 5) of the elastic head 24 makes contact with the end cap face 26 initially, and as the head is compressed, contact gradually continues toward the center until the center portion 17 (see FIG. 5) of the elastic head 24 makes contact. Thus, the entire fluid sample is evacuated, unless an o-ring is present.

Figure 6:
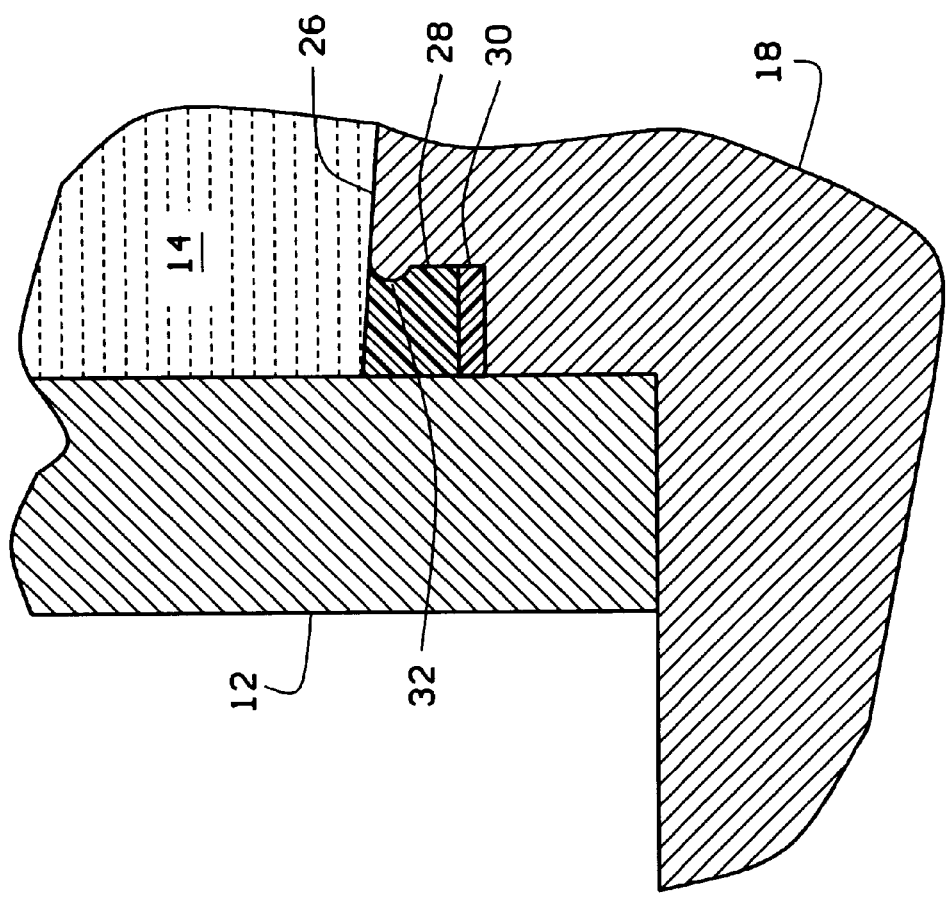
FIG. 6 is a detailed cross-sectional view of the elastomeric seal between the end cap and the cylinder body of the present sample cylinder.

To completely ensure that no sample material is retained in the o-ring groove of the end cap 18, the end cap is adapted to co-axially receive a gasket seal 28 instead of an o-ring. Gasket seal 28 completely fills the void between the end cap 18 and the cylinder body 12. Therefore, there is no unfilled groove in the end cap 18 which could retain fluid. FIG. 6 shows a close up view of the seal 28. It is preferable that beneath the main seal 28 is a back up seal 30 made of a firm material such as a hard rubber or plastic. The main seal 28 may be made of the same material as the elastomeric piston head 24 or any similar material.

To help retain the seal 28 in place, the end cap 18 may include a small notch 32 near the inner face 26. The seal is then packed between the end cap 18 and the cylinder body 12 so that a portion thereof fills in the area underneath the notch 32. When the piston head 24 contacts the end cap 18 there is no space between the end cap 18 and the cylinder body 12 which could hold fluid.

While the foregoing is directed to the preferred embodiments of the present invention, other and further embodiments of the invention may be devised without departing from the basic scope thereof, and the scope thereof is determined by the claims which follow.

What is claimed is:

1. A vanishing head sample cylinder comprising:

a hollow cylindrical body open at one end defining a sampling chamber having an interior wall therein and having an axis;

a piston disposed within said body, axially freely movable within the body;

a sampling end cap closing the open end, having a first surface facing an interior volume of the hollow body;

an outlet through said end cap for communicating the interior volume to an exterior of the cylinder; and an axially compressible elastic head affixed to the piston, said head having a head surface exposed to the sample chamber that faces the end cap and the head surface having a center portion axially aligned with the outlet and said center portion being further from the end cap first surface than is an outer portion of the head surface wherein the elastic head gradually increases in axial thichness from the center portion to the outer portion of the head surface, whereby as the piston is displaced axially toward the end cap, any material within the interior volume of the hollow body is more completely forced through the outlet of the end cap as the elastic head is compressed against the facing first surface of the end cap.

2. The vanishing head sample cylinder of claim 1, wherein the outlet through the end cap has a cylindrical axis aligned with the center portion of the elastic head.

3. The vanishing head sample cylinder of claim 2, wherein the contour of the head surface of the elastic head is curved concave and facing the end cap.

4. The vanishing head sample cylinder of claim 1, where the end cap has a concave first surface facing the piston.

5. The vanishing head sample cylinder of claim 4, wherein the concavity of the facing first surface is curved.

6. The vanishing head sample cylinder of claim 4, wherein the concavity of the facing first surface is frusto-conical.

7. The vanishing head sample cylinder of claim 4, wherein the outlet of the end cap and the center portion of the head surface are aligned.

8. The vanishing head sample cylinder of claim 4, where the outlet of the end cap is axially centered about an apex of the concave first surface.

9. The vanishing head sample cylinder of claim 8, where and the outlet of the end cap having a cylindrical axis aligned with the center portion such that the outlet is at a maximum axial distance from the head surface of the elastic head of the piston.

10. The vanishing head sample cylinder of claim 1, further comprising a seal disposed between the end cap and the interior wall of the hollow cylindrical body providing a complete gapless contact between a radial edge of the facing surface of said end cap and the interior wall of the cylindrical body so as to minimize trapping of any residual material between the seal and the elastic head when the piston moves fully toward the end cap.

11. The vanishing head sample cylinder of claim 10, wherein the seal further comprises a gasket-like back up seal portion and an inwardly flanged ring main portion, both fitting in a notched recess of the end cap thereby eliminating any gaps between the gasket and flange ring portions where residual material may remain upon full movement of the piston toward the end cap.

* * * * *